(12) United States Patent
Leduc et al.

(10) Patent No.: US 11,786,881 B2
(45) Date of Patent: Oct. 17, 2023

(54) METHOD AND SYSTEM FOR PRODUCING SUBSTANTIALLY MONO-DISPERSE PARTICLES OF A SUBSTANCE

(71) Applicant: NANOMI, B.V., Oldenzaal (NL)

(72) Inventors: Lucie Anne Aude Leduc, Oldenzaal (NL); Robertus Franciscus Duwel, Oldenzaal (NL); Miriam Girones Nogue, Oldenzaal (NL); Gerrit Jan Veldhuis, Hengelo (NL)

(73) Assignee: NANOMI B.V., Oldenzaal (NL)

( * ) Notice: Subject to any disclaimer, the term of this patent is extended or adjusted under 35 U.S.C. 154(b) by 323 days.

(21) Appl. No.: 16/605,991

(22) PCT Filed: Apr. 18, 2018

(86) PCT No.: PCT/IB2018/052690
§ 371 (c)(1),
(2) Date: Oct. 17, 2019

(87) PCT Pub. No.: WO2018/193389
PCT Pub. Date: Oct. 25, 2018

(65) Prior Publication Data
US 2021/0138421 A1    May 13, 2021

(30) Foreign Application Priority Data

Apr. 19, 2017   (NL) ..................................... 2018744

(51) Int. Cl.
*A61K 9/16* (2006.01)
*B01F 23/00* (2022.01)
(Continued)

(52) U.S. Cl.
CPC ............. *B01J 13/08* (2013.01); *A61K 9/1682* (2013.01); *B01D 11/0492* (2013.01);
(Continued)

(58) Field of Classification Search
CPC .. A61K 9/1647; A61K 9/1682; A61K 9/5031; A61K 9/5089; B01D 11/04;
(Continued)

(56) References Cited

U.S. PATENT DOCUMENTS

2007/0227591 A1   10/2007   Wissink et al.
2009/0104274 A1    4/2009   Khopade et al.
2009/0297621 A1   12/2009   Lim et al.

FOREIGN PATENT DOCUMENTS

EP        1755773 B1 *  7/2010   .......... B01F 13/0059
WO    2005115599 A1    12/2005

OTHER PUBLICATIONS

Baker, RW. (Membrane Technology and Applications 2012, John Wiley & Sons, pp. 167, 299 and 319) 2 page total). (Year: 2012).*

\* cited by examiner

*Primary Examiner* — Ernst V Arnold
(74) *Attorney, Agent, or Firm* — THE WEBB LAW FIRM (57) ABSTRACT

Provided herein is a first fluid dispersed in a second fluid to form an emulsion of micro-droplets having an average droplet size and having a droplet size distribution around the average droplet size and below a maximum droplet size. The micro-droplets will lose their solvent to transform to micro-spheres exhibiting a particle size distribution around an average particle size and substantially below a maximum allowable particle size. The micro-spheres are subjected to a micro-filter having a relatively narrow pore size distribution around an average pore size, which average pore size is between the average particle size and the maximum particle size. A filtrate of the micro-filter comprises a majority of the micro-spheres that is substantially void of micro-spheres having a particle size exceeding the maximum allowable particle size.

19 Claims, 4 Drawing Sheets

(51) Int. Cl.
  *B01F 23/41* (2022.01)
  *B01J 13/08* (2006.01)
  *B01D 11/04* (2006.01)
  *B01D 39/10* (2006.01)
  *B01F 25/314* (2022.01)
  *B01F 33/302* (2022.01)
  *B01F 101/22* (2022.01)

(52) U.S. Cl.
  CPC .......... B01D 39/10 (2013.01); B01F 23/4105 (2022.01); B01F 25/3142 (2022.01); B01F 33/302 (2022.01); *B01F 2101/22* (2022.01)

(58) Field of Classification Search
  CPC . B01D 11/0492; B01D 39/10; B01F 2101/22; B01F 23/41; B01F 23/4105; B01F 25/3142; B01F 33/302; B01J 13/08; B01J 2/06
  See application file for complete search history.

METHOD AND SYSTEM FOR PRODUCING SUBSTANTIALLY MONO-DISPERSE PARTICLES OF A SUBSTANCE

CROSS-REFERENCE TO RELATED APPLICATIONS

This application is the United States national phase of International Application No. PCT/IB2018/052960 filed Apr. 18, 2018, and claims priority to Netherlands Patent Application No. 2018744 filed Apr. 19, 2017, the disclosures of which are hereby incorporated by reference in their entirety.

BACKGROUND OF THE INVENTION

The present invention relates to a method of producing substantially mono-disperse particles of a substance. The invention moreover relates to a system to produce these particles. Mono-disperse particles are intended to designate a population of particles with substantially a same particle or grain size, i.e. exhibiting an extremely narrow particle size distribution among the population. Although not exclusively, the present invention particularly pertains to a method for producing mono-disperse particles with pharmaceutical formulations suitable for targeting particular tissue and/or organ(s) in a living body with a formulated active ingredient, for example when administered upstream of the target organ or tissue in the vascular system of a patient.

Most medicines/pharmaceuticals are administered systemically, for example orally, intravenously, by vaccine, intramuscularly or the like. Nevertheless, when appropriate, it would be advantageous to be able to deliver the pharmaceutical primarily to a diseased tissue or organ, because this would reduce the dose required and also minimize side effects. This could be of particular relevance for instance, for the administration of growth factors and cytokines capable of activating the growth and differentiation of resident stem cells in a particular tissue. Because of the potent biological activity of these molecules, it would be desirable to limit their action to the intended tissue, with minimal or no spillover to the rest of the body.

Also for the delivery of cancer chemotherapeutic agents local delivery of an appropriate cytostatic drug would be most favourable because if the cancerous tissue could be targeted specifically then it may allow the administration of higher doses to the targeted cells while minimizing the terrible toxic side effects of the same, at least to a significant extent.

In more acute situations such as in heart attacks and strokes better treatments may be possible, particularly those directed to regenerate the damaged tissue, if the organs affected could be specifically targeted. In chronic situations, such as Parkinson disease, diabetes, or pulmonary fibrosis, local administration of agents capable to reconstitute the deficient cell type(s) have the potential to improve the prognosis of the disease.

In regenerative medicine an interesting strategy for local tissue regeneration is the administration of substantially mono disperse micro-spheres to the blood supply of the targeted site, said micro-spheres being loaded with a suitable growth factor. The aim is that the particles are of such average size that they will get stuck in the capillary bed of the targeted site, like for instance an organ or muscle, and gradually release the relevant growth factor. The size distribution of the micro-spheres concerned should in that case be so narrow that only a negligible part of the micro-spheres can pass the capillary bed to be systematically lost, while, even more importantly, no micro-spheres should be so large that they will block the pre-capillaries of the target site as this may cause macro-infarcts.

SUMMARY OF THE INVENTION

The aim of the present invention is inter alia to provide a method and/or system that allows particles to be produced with an extremely narrow particle size distribution, which renders these particles particularly suitable for such local delivery of pharmaceutical agents in a human or animal body. An important recognition underlying the invention is that it is of the utmost importance that particles above a certain size should be absolutely absent in the end product of such a method, while the method should preferably also be both economical and efficient with regard to the consumption of source material. Particularly in case of certain pharmaceutical drugs and bio-technological products, said source material may be extremely valuable or expensive.

In order to achieve said object a method of producing a substantially mono-disperse particles of a substance in accordance with the present invention is characterized by comprising the steps of: dissolving said substance in a solvent to form a first fluid containing said substance; dispersing said first fluid in at least one second fluid to form an emulsion of micro-droplets containing said first fluid in a second fluid, said micro-droplets having an average droplet size and having a relatively narrow size distribution around said average droplet size and below a maximum droplet size; allowing said micro-droplets containing said first fluid to lose said solvent in said second fluid and to turn into micro-spheres containing said substance in said second fluid, said micro-spheres exhibiting a relatively narrow size distribution around an average particle size and substantially entirely below a maximum allowable particle size; subjecting said second fluid containing said micro-spheres to a micro-filter having a relatively narrow pore size distribution around an average pore size, which average pore size is between said average particle size and said maximum allowable particle size; and obtaining a filtrate that comprises a majority of said micro-spheres and that is void of micro-spheres having a particle size exceeding said maximum allowable particle size.

In another embodiment of the present invention provides method of producing micro-spheres of a substance comprising the steps of: a. dissolving said substance in a solvent to form a first fluid containing said substance; b. dispersing said first fluid in at least one second fluid to form an emulsion of micro-droplets of said first fluid in a second fluid, said micro-droplets having an average droplet size and having a droplet size distribution around said average droplet size and below a maximum droplet size; c. allowing said micro-droplets of said first fluid to lose said solvent in said second fluid and to form micro-spheres containing said substance in said second fluid, said micro-spheres having an average particle size and having a particle size distribution around said average particle size and below a maximum particle size; d. subjecting said second fluid containing said micro-spheres to a micro-filter having a relatively narrow pore size distribution around an average pore size, which average pore size is between said average particle size and said maximum particle size to form a filtrate comprising a majority of said micro-spheres that is substantially void of micro-spheres having a particle size exceeding the maximum allowable particle size.

The method according to the invention first of all creates an emulsion of micro-droplets containing a first fluid of said substance. This first fluid provides a uniform and homogenous distribution of said substance over said micro-droplets, i.e. these droplets will contain said substance in the same concentration. The droplet size may be controlled to a very high level while forming such an emulsion, for instance by applying the method that is described in published European patent application EP 1.755.773 by applicant, which contents is incorporated herein by reference. As a result the size distribution can be made extremely narrow around an average droplet size. The micro-spheres created by this method will accordingly share a similar sharp size distribution around an average particle size that is substantially below a maximum allowable particle size. In general a relatively narrow or sharp particle size distribution is accomplished according to the invention by using a generation and filtration device that has been manufactured with the aid of photolithography or similar extremely accurate and controllable techniques as applied in e.g. nowadays semiconductor technology.

In a next step of the process the largest particles that exceed said maximum allowable particle size are removed by filtering said micro-spheres over a micro-filter having a relatively narrow pore size distribution around an average pore size that is between said average particle size and said maximum allowable particle size to yield a filtrate that is void of particles that exceed said allowable size. Due to both the specific creation step and the specific filtration step that are used in this method for forming particles hardly no source material is wasted. Substantially all particles will have approximately a same size resulting in a similar efficacy, while no particle will have a particle size that exceeds said maximum allowable particle size.

It should be noted that although the invention refers to micro-spheres that are created in the second fluid, these micro-spheres need not be exactly mathematically spherical. Also the micro-spheres may reside either in liquid or solid form in the second fluid after the solvent has been expelled from the micro-droplets. The term "micro-sphere" as used herein is interchangeable with "particle" "micro-particle" or "micro-spherical particle" and refers to particles in the size range (average length, width or diameter) from submicron to millimeter. The known particle size analysis methods are suitable for determining the particle size, for example using Coulter Counter, Laser Diffraction Particle Size Analyzer or CPS disc centrifuge.

Although the micro-spheres obtained by the method according to the invention may be kept in a suspended, or at least wet, state, a preferred embodiment of the method according to the invention is further characterized in that said micro-spheres comprise solid micro-particles, in that said filtrate dried to remove said second fluid from said micro-particles, and in that said micro-particles are collected to obtain a dry powder of solid micro-particles. As a result of such drying step the solid micro-spherical particles are rendered into a form of a dry mono-disperse powder that will feature a long shelve-life of the relevant material together with a low weight and volume.

The particles obtained by the method specifically qualify for in vivo local drug delivery. To that end a specific embodiment of the method according to the invention is characterized in that said substance comprises a pharmaceutically active agent. Such a pharmaceutical product may be in pure form or linked, embedded or otherwise loaded to a carrier. As such a further specific embodiment of the method according to the invention is characterized in that said substance comprises a polymer. The polymer may be employed as a carrier matrix that captures, encapsulates, binds or otherwise contains the actual agent that is to be released onsite or may, alternatively, be the pharmaceutically active agent itself. In either case a controlled and extended in vivo release over time of the pharmaceutical product concerned may be effected by a further specific embodiment of the method according to the invention that is characterized in that said polymer is biocompatible and/or biodegradable. The examples of polymer include poly(glycolic acid), poly(d,l-lactic acid), poly(l-lactic acid), copolymers of the foregoing, and the like.

Once the micro-droplets are formed in the second fluid it is important to prevent them from aggregating. To that end a further preferred embodiment of the method according to the invention is characterized in that said second fluid comprising a surfactant substantially preventing said micro-droplets from aggregating. As a result the mono disperse nature of the droplets is being maintained in the second fluid. A specific embodiment of the method according to the invention, in this respect, is characterized in that said surfactant is polyvinyl alcohol, and that said second fluid is an aqueous solution.

There are different ways of producing an emulsion of micro-droplets. However, according to the invention, a preferred embodiment of the method according to the invention is characterized in that said micro-droplets are generated by injecting said first fluid in at least one micro-channel of a micro-channel device, said micro-channel having a cross-sectional diameter of a specific size and having an outlet, and by ejecting droplets that emerge at said outlet of said at least one micro-channel in said second fluid. Specific embodiments of micro-channel devices that may be employed this way for the formation of micro-droplets are described in European patent application EP 1.755.773 by applicant that is incorporated herein by reference.

Specifically the method according to the invention embraces an embodiment that is characterized in that said micro-channel device comprises a channel plate that comprises said at least one micro-channel, in that said outlet delivers said droplets at an output surface of said channel plate, and in that said channel plate comprises at least one secondary channel that extends between a first end below an inlet surface and opening within said micro-channel and a second end that opens to said output surface of said channel plate, wherein more particularly said secondary channel extends the channel from said inlet surface to below said output surface in open communication with said micro-channel. Such a device appears to generate micro-droplets with an extremely stable, i.e. constant, reproducible diameter resulting in an emulsion in which the droplets are to a high degree equal to one another. This mono-disperse nature of the droplet formation is further enhanced by a specific embodiment of the method according to the invention that is characterized in that said secondary channel has a corrugated wall extending towards said outlet or outlet surface, particularly having toothed corrugations.

Specifically a further embodiment of the method according to the invention is characterized in that said micro-channel device comprises a micro-sieve, and more particularly in that said first fluid is injected in said second fluid through a micro-sieve that has strictly defined micro-channel defining pores that are determined photo-lithographically. The pores that define the micro-channels that guide the first fluid into the second fluid may be formed in several ways, like for instance by means of etching using photo-lithographic masking techniques or by means of a lift-off process following deposition on a photo-lithographically determined pattern. A specific embodiment of the method of the invention in that respect is characterized in that that said micro-sieve comprises a solid substrate carrying a sieve layer or filter layer, said pores being etched in said sieve layer or filter layer, and said solid substrate having a least one window underneath said sieve layer or filter layer that exposes an area of said sieve layer or filter layer that comprises at least a number of said pores, and more particularly in that said solid substrate comprises silicon. This way regular semiconductor technology may be used to produce an extremely precise micro-channel device, well within feasible tolerances for the production of mono-disperse micro-droplets by the method according to the invention.

Like the injection device, also the micro-filtered employed in the method according to the invention preferably comprises a sieve layer or filter layer having strictly defined pores that are formed using photo-lithographic etching and/or deposition techniques, for instance by etching or a lift-off process. Also the sieve layer or filter layer of the micro-filter preferably comprises a solid layer of a material that is compatible with off the shelve semiconductor technology.

In a practical setup the method of the invention is characterized in that said second fluid is passed along a first surface of said micro-filter, while said filtrate, comprising said micro-spheres, is collected at a second, opposite surface of said micro-filter. This setup has the advantage that the second fluid can be kept in a closed circulation of a relatively small volume of liquid, while the micro-spheres of a size below said maximum allowable level are constantly furnished and extracted at said outlet surface of the filter. A more specific embodiment, in that respect, of the method is according to the invention characterized in that said second fluid is circulated over said first surface by means of first pump means in an aseptic closed circulation and in that said filtrate is evacuated from said second surface by means of aseptic second pump means through a further filter that collects the micro-spheres present in said filtrate, while a filtrate of said further filter is feedable to said closed circulation. The liquid phase of the extracted fluid, in this case, may be fed back to the primary circuit after the micro-spheres have been removed and harvested from said fluid. In order to avoid any harm to the vulnerable micro-spheres, specifically in order not to distort their mono-disperse individual size, a further preferred embodiment of the method according to the invention is thereby characterized in that said first and second pump means are any pump, including, but not limited to peristaltic pump, centrifugal pump, gear pump and piston pump. The use of peristaltic pump means avoids the risk of mechanical impacts on the particles that could deteriorate the integrity of the mono-disperse particles concerned while peristaltic pump means, moreover, offer a closed environment to the internal fluid flow that may be kept aseptic as a result of that.

The method is preferably performed as a continuous process without noticeable interruptions. This inter alia requires a proper functioning of the micro-filter throughout the process. To that end a further preferred embodiment of the method according to the invention is characterized in that that said micro-filter is provided with back-flush means. These back-flush means can be devised in many ways. A specific embodiment of the method according to the invention that has proven successful in this respect is characterized in that said back-flush means are coupled to said second opposite surface of said micro-filter and comprise a controllable valve that is used to release a pressurized gas, particularly an inert gas like a noble gas or nitrogen gas, onto said opposite second surface of said micro-filter, while an alternative embodiment of the method according to the invention is characterized in that said back-flush means comprises a peristaltic pump that is used to create a flow from said second opposite surface across said micro-filter.

The method according to the invention offers a wide process window as far as the target size of the mono-disperse particles is concerned. A wide range of micro to sub-micro sized mono-disperse particles may be obtained by adapting the dimensions of the injections means, that will deliver the micro-droplets, and the dimensions of the pores in the micro-filter to one another and to tune these dimensions to the desired target size of the particles concerned. In this respect, but without limitation, a specific embodiments of the method according to the invention is characterized in that said micro-filter has an average pore size of between 5 and 200 microns together with a pore size distribution within a standard deviation of between 0, 1 and 5 microns around said average pore size, and in that said micro-spheres have an average particle size of between 5 and 150 microns, preferably between 10 and 125 microns, more preferably between 12.5 and 100 microns, together with a particle size distribution within a standard deviation of between at most 25%, preferably at most 15%, even more preferably at most 10%, and said particle size distribution is 85%, preferably more than 90%, even more preferably more than 95% below the average pore size of said micro-filter.

The invention further relates to a system for producing particles of a substance that might inter alia be used to implement the method according to the invention in one or more of its embodiments described hereinbefore. According to the invention a system for producing substantially mono-disperse particles of a substance is characterized by comprising means for forming an emulsion of substantially mono-disperse micro-droplets containing a first fluid in a second fluid, said micro-droplets exhibiting a relatively narrow size distribution around an average size and substantially below a maximum allowable particle size, filtration means having a filter pores of substantially narrow pore size distribution that is between said average particle size and said maximum allowable particle size, and by collection means to collect a fraction of said micro-spheres in said emulsion having a particle size below said maximum allowable particle size.

BRIEF DESCRIPTION OF THE DRAWINGS

The invention will hereinafter be described in further detail with reference to a few examples and along the lines of a drawing. In the drawing.

It is noted that figures are pure schematic and not drawn to scale. Particularly some dimensions may be more or less exaggerated to improve the overall intelligibility. In the drawing, like parts are designated with a same reference numeral.

DETAILED DESCRIPTION OF THE INVENTION

Example I

Figure 1:
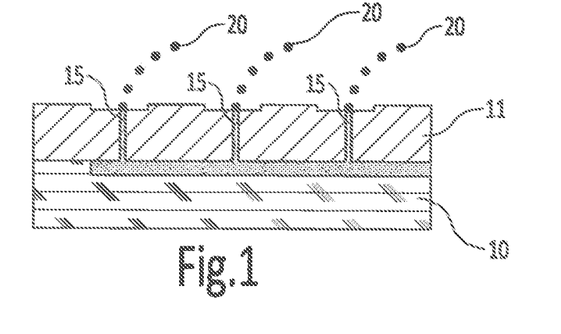
FIG. 1: a schematic representation of an injection device that can be used in the method according to the invention for the formation of an emulsion of substantially mono-disperse micro-spheres.

A substance is dissolved, in solid or liquid form, in a solvent to obtain a homogeneous first fluid of said substance. In this example the substance comprises polycarbonate and said substance is dissolved in di-chloro-methane (DCM, or methylene chloride) as the solvent. Using an injection device for instance as is shown in FIG. 1, said first fluid is subsequently injected in a second fluid to form an emulsion of said first fluid in said second fluid. In this example demineralized water is used as said second fluid. This will create micro-droplets of polycarbonate solution (first fluid) that are dispersed in water. The micro-droplets will lose the solvent while they are submersed in water to form practical identical polycarbonate micro-spheres.

Although in principle a wide variety of devices may be used for the above emulsification step, preferably use is made of an injection device as described in the aforementioned patent application by applicant. The contents of that application is incorporated herein by reference and provides further details on how to obtain a mono-disperse emulsion of micro-droplets in a (second) fluid.

The injection device used in this example comprises a micro-channel device that comprises a micro-sieve layer on a silicon substrate 10 having a number of injection channels that are defined photo-lithographically by an etch mask and are etched using said mask in said sieve layer using regular semiconductor production techniques with which a skilled person is assumed to be familiar with. This will create micro-channels with a strictly defined diameter that are identical to one another within extremely small tolerances as are associated with semiconductor technology. The sieve layer may comprise a semiconductor material such silicon or a material like silicon nitride or silicon oxide, all of which are compatible with nowadays advanced semiconductor processing techniques.

Figure 3:
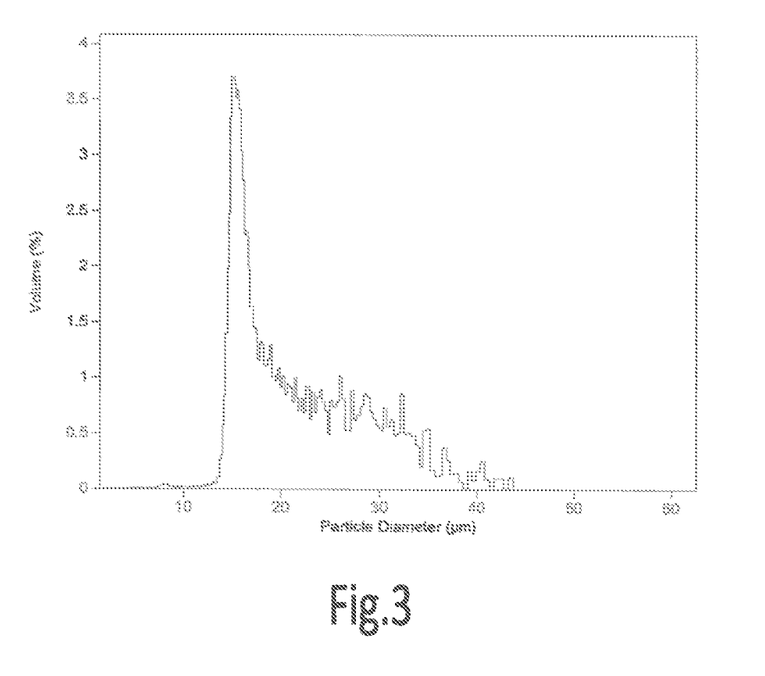
FIG. 3: an exemplary particle-size distribution of the micro-spheres obtained by the injection device of FIG. 1.

Said high precision of said micro-channel device translates into the generation of a collection of micro-droplets 20 that are likewise substantially identical to one another, i.e. having about the same size and form. After the micro-droplets have lost their solvent, the resulting micro-spheres of polycarbonate will equally share such a relatively sharp, well defined particle size distribution around an average particle size and almost completely below a maximum allowable particle size. In this example, the micro-channels all have a diameter of 15 microns to generate solid poly-carbonate micro-spheres having almost all a same size of between 10 and 40 microns around an average size of around 15-16 microns as illustrated by the size distribution that is shown in FIG. 3. The maximum allowable particle size is 30 microns in this example.

Figure 2:
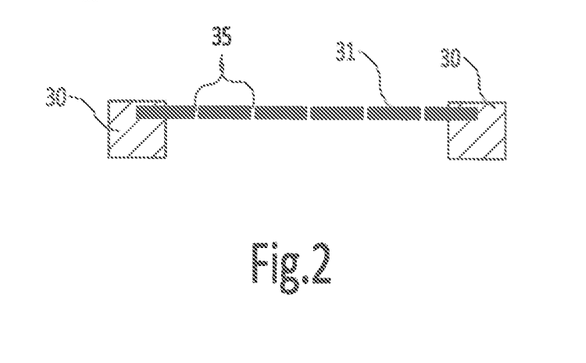
FIG. 2: a schematic representation of an micro-filter device that can be used in the method according to the invention to render a collection of substantially mono-disperse micro-spheres that are all below a maximum allowable particle size.

Inevitably also some micro-droplets 20 will be produced that have a larger size than said target size of around 15 microns, as illustrated by the tail of the particle size distribution of FIG. 3 that comprises around 4% of all micro-droplets that were produced. In order to avoid particles in the targeted end product that have a particle size exceeding the maximum allowable particle size of 30 microns, the emulsion containing said micro-spheres is subjected to a micro-filtration process with a micro-filter like the one shown in FIG. 2. Like the injection device that is used according to the invention, such as the one shown in FIG. 1, also the micro-filter has been produced using high precision techniques resulting in a filter layer having precisely defined and configured filter pores. As such the micro-filter may comprise a micro-sieve layer like the one that is used as an injection device framed in a support 30 or, like in this example, a metal layer with almost identical perforations or openings that has been created by a lift-off process following semiconductor processing of an appropriate mould.

Figure 4A:
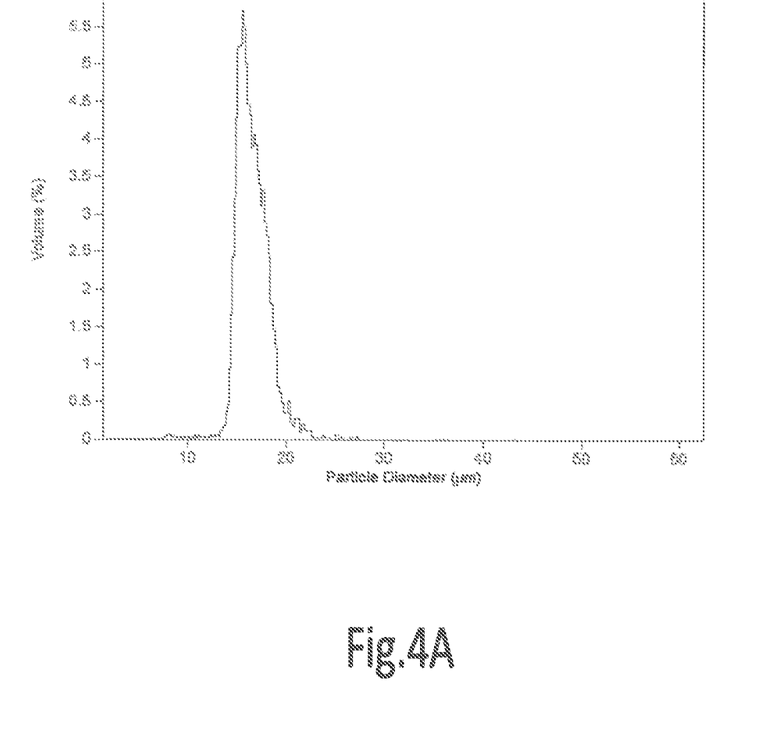
FIG. 4A: an exemplary particle-size distribution of micro-particles obtained after filtration with the micro-filter device of FIG. 2.
Figure 4B:
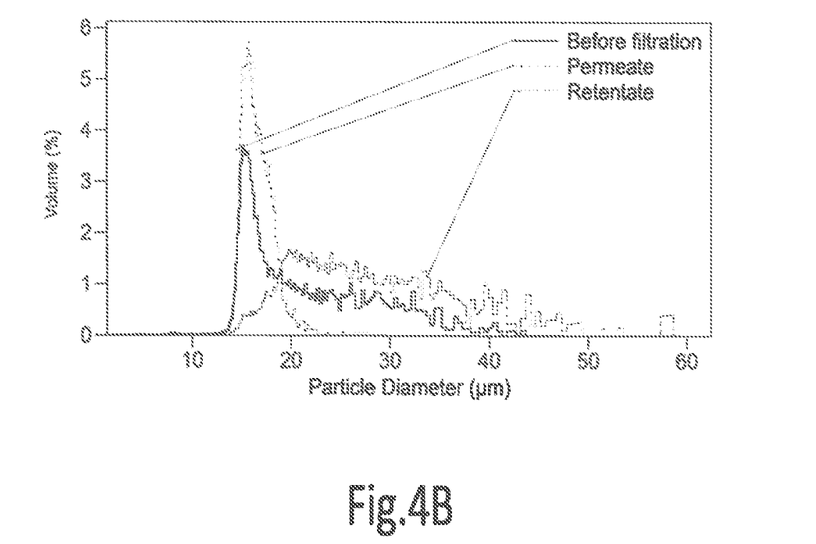
FIG. 4B: a comparison of particle-size distribution of micro-particles.

As a result of the high precision of its formation, the filter layer exhibits an extremely narrow filter pore size distribution around an average pore size, which average pore size is between said average particle size and said maximum allowable particle size. In this example, the pores or perforations in the metal layer share such average diameter of approximately 20 microns. This micro-filter is used as a cross-filter to process the fluid containing the poly-carbonate micro-spheres that was created by means of the injection device of FIG. 1. After 15 minutes of filtration, the resulting filtrate/permeate that is collected from said micro-filter features a particle size distribution as shown in FIG. 4A. This product contains no particles having a particle size exceeding said maximum allowable particle size of 30 microns as every particle of that size will not have passed the filter, while almost all particles that have been produced are retained in the ultimate filtrate due to both the narrow size distribution of particle formation in combination with the narrow size distribution of particle filtration. In practice a yield or efficiency of more than 99% is achieved in this respect in terms of practical use of the source product. A comparison of particle-size distribution of micro-particles, obtained by the injection device (i.e. before micro-filtration), obtained after micro-filtration (i.e. permeate and retentate) is shown in FIG. 4B.

Example II

Figure 5:
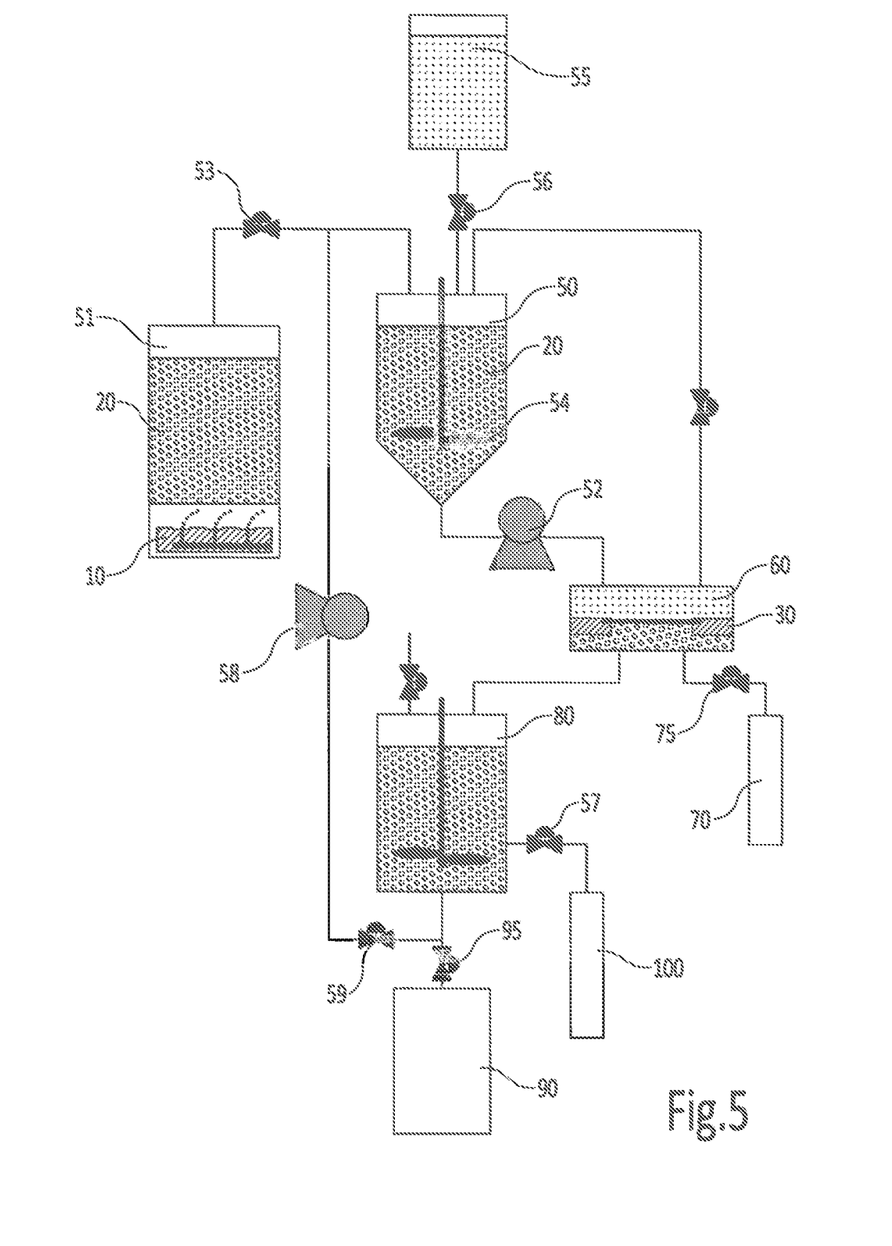
FIG. 5: a schematic representation of a practical setup at start up of a system according to the invention that is particularly suitable for carrying out the method according to the invention.
Figure 6:
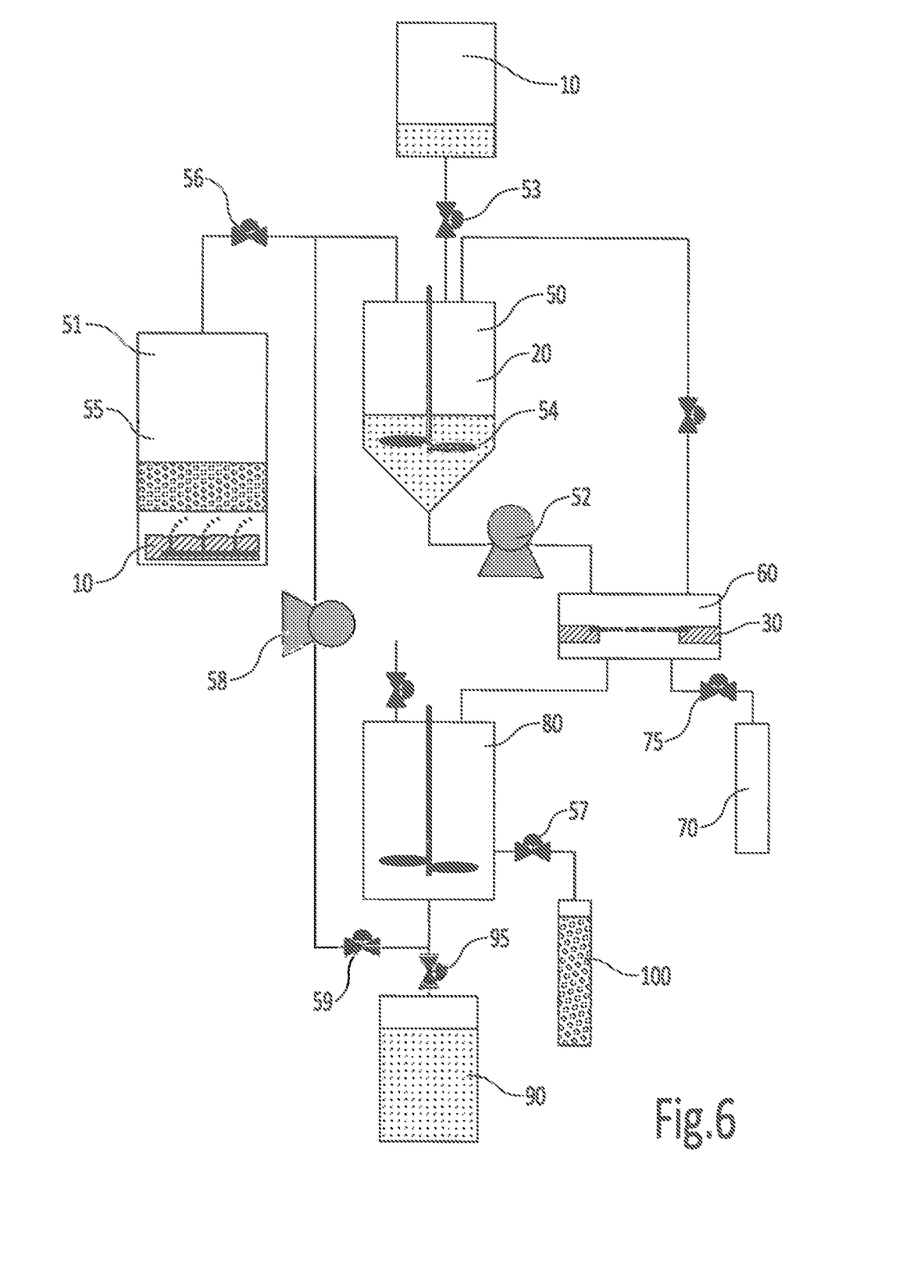
FIG. 6: a schematic representation of the setup of FIG. 5 after carrying out the method according to the invention.

A practical and exemplary setup for carrying out the method according to the invention is shown in FIGS. 5 and 6. In this example, this setup will be used for the formation of biodegradable micro-particles. More particularly, these biodegradable particles comprise a biodegradable polymer that is loaded or linked with a pharmaceutically active agent. A suitable biodegradable and bio-absorbable polymer can be taken from a wide variety of polymers and co-polymers based on poly (L and/or D) lactide. This polymer will slowly degrade and dissolve while being in an aqueous environment as will be experienced in the living body and has moreover proven to be bio-compatible to avoid inflammatory response. By loading or linking a pharmaceutical agent in such a biodegradable polymer (matrix) a gradual local release of said agent may be realized at a specific site in the body, which renders these biodegradable particles particularly useful for treating local injuries, like in regenerative medicine. The growth factor used in such treatments, however, are extremely expensive so material losses of such substances need to be kept at a minimum, if wasted at all. The method and setup of the invention specifically address these and other requirements.

An appropriate amount of the starting biodegradable polymer material that is loaded with the active agent is dissolved in di-chloro-methane as a solvent, although also other solvents may be applied like for instance tetra-hydro-furan (THF) and ethyl-acetate-butyl. The first fluid is injected in water as a secondary fluid phase using an injection device 10 as described above to create an emulsion of almost mono-disperse micro-droplets 20 having an average droplet size of around 15 microns and a sharp size distribution around that average size. A few percent poly-vinyl alcohol (PVA) has been added to the water as a surfactant that will prevent aggregation of the micro-droplets that are collected in this water phase. The solvent from the micro-droplets is then extracted to obtain solvent free micro-spheres of polymer loaded with the active agent. Once the extraction is finished, the micro-spheres are not droplets anymore but solid micro-particles. The emulsion of (almost) mono-disperse micro-particles is created and, if necessary, temporarily kept in a container 51 and may be transferred to a process vessel 50 by operation of a control valve 53. The process vessel 50 is part of a practical setup according to the invention that may be used to carry out the method according to the invention and that will be explained further hereinafter.

The process vessel 50 comprises stirring means, illustrated by the rudder 54 in FIG. 5, to keep the emulsion of micro-particles suspended. In order to maintain a sufficient aqueous environment water or a 0.05% polysorbate 20 (Tween®20) solution in water may be added to this emulsion as demanded from an auxiliary vessel 55 by opening a control valve 56 that has been provided for this purpose.

Connected to the process vessel 50 is a peristaltic pump 52 that will circulate the emulsion over a primary side of a cross-filter 60 and back to the vessel 50 again. The cross-filter comprises a micro-filter 31 of the type as described hereinbefore with a cut-off pore size of 17 microns. After 90 minutes of filtering, the filtrate of this filter exhibits a particle size distribution, containing no particles exceeding a maximum allowable particle size of 20 microns, while more than 99% of the initial product/sub stance is retained in said filtrate. Economical losses due to inadvertent waste of expensive polymer product, are hence kept to a minimum.

To prevent the micro-filter from blocking due to oversized particles stuck in the filter pores, back-flush means are provided. The back-flush means comprise a cylinder 70 of pressurized gas that may be released onto the second opposite surface of the micro-filter by operating a control valve 75. Although many gasses may be used for this purpose, including regular gasses like carbon dioxide and air, preferable an inert gas such as nitrogen or a noble gas like helium or argon is being used in order to avoid any reaction with the product. The control valve 75 is periodically opened for a short while to exert a back-pulse of gas through the pores of the filter that will lift any particles sticking in the filter such that they will be taken up by the main liquid stream that flows over the other side of the filter to be returned to the vessel.

The filtrate of the cross-filter 60 is concentrated by a further filter 80 in order to capture and collect all micro-particles from the filtrate of the micro-filter 31. In this example this further filter 80 comprises a micro-membrane filter that will capture virtually all solid particles resident in the filtrate of the micro-filter 31. Any appropriate filter that is commercially available may be used for this purpose, like for instance the Amicon® range of ultra-filters by Merck Millipore. In a normal mode of operation a control valve 59 to a second peristaltic pump 58 is in the closed position and a valve 95 to a waste vessel 90 is open. The aqueous filtrate output of the filter 80 is collected in the waste vessel 90. Finally, by appropriate setting of the valves 57, 59, 95 a back-flush pulse is given using a second peristaltic pump 58 to force the valuable retentate that accumulated on the filter 80 surface into a product container 100.

The retentate of the ultra-filter contains the precious micro-particles. This product is freeze dried to form a mono-disperse powder of solid particles of the biodegradable polymer that contains the active pharmaceutical agent, like for instance a growth factor or a cytostatic agent. Due to the selective choice of both the injection means for creating an emulsion containing these particles as substantially mono-disperse micro-spheres as well as the filtration means for post-processing this, the resulting product is to an extreme extent mono-disperse in that virtually all particles have the same size and, more importantly, the resulting product is safe in that (virtually) no particle will have a size that exceed a maximum allowable size.

Although the invention has been described in further detail with reference to these embodiments only, it will be understood that the present invention is by no means limited to the embodiments given. On the contrary a skilled person may conceive many more alternatives, variations and further embodiments without departing from the scope and spirit of the present invention.

The invention claimed is:

1. A method of producing micro spheres of a substance comprising the steps of:
   a. dissolving said substance in a solvent to form a first fluid containing said substance;
   b. dispersing said first fluid in at least one second fluid to form an emulsion of micro droplets of said first fluid in a second fluid, said micro droplets having an average droplet size and having a droplet size distribution around said average droplet size and below a maximum droplet size, said micro droplets generated by a micro-channel device comprising a micro sieve comprising: a channel plate comprising at least one micro-channel having a cross-sectional diameter of a specific size and having an outlet, and at least one secondary channel;
   c. allowing said micro droplets of said first fluid to lose said solvent in said second fluid and to form micro spheres containing said substance in said second fluid, said micro spheres having an average particle size and having a particle size distribution around said average particle size and below a maximum particle size; and
   d. subjecting said second fluid containing said micro spheres to a micro filter having a relatively narrow pore size distribution around an average pore size, which average pore size is between said average particle size and said maximum particle size to form a filtrate comprising a majority of said micro spheres that is substantially void of micro spheres having a particle size exceeding a maximum allowable particle size.

2. The method according to claim 1, wherein said substance comprises a polymer.

3. The method according to claim 2, wherein said substance further comprises a pharmaceutically active agent.

4. The method according to claim 2, wherein said polymer is biodegradable.

5. The method according to claim 1, wherein said second fluid comprises a surfactant substantially preventing said micro droplets from aggregating.

6. The method according to claim 5, wherein said surfactant comprises polyvinyl alcohol, and that said second fluid is an aqueous solution.

7. The method according to claim 1, wherein step (d) is followed by drying said filtrate to remove said second fluid from said micro spheres and collecting said micro spheres to obtain a powder.

8. The method according to claim 1, wherein said at least one secondary channel has a corrugated wall extending towards said outlet.

9. The method according to claim 1, wherein said micro sieve has strictly defined pores determined photo lithographically.

10. The method according to claim 9, wherein said micro sieve comprises a solid substrate carrying a filter layer, said pores being etched in said filter layer and said solid substrate having a least one window underneath said filter layer that exposes an area of said filter layer that comprises at least a number of said pores.

11. The method according to claim 10, wherein said solid substrate comprises silicon.

12. The method according to claim 1, wherein said micro filter comprises a filter layer having strictly defined pores that are formed using photo lithographic etching and/or deposition techniques.

13. The method according to claim 12, wherein said filter layer is a metal layer having openings that are created by means of lift off process.

14. The method according to claim 1, wherein said second fluid containing said micro spheres is passed along a first surface of said micro filter, while said filtrate, comprising said micro spheres, is collected at a second opposite surface of said micro filter.

15. The method according to claim 14, wherein said micro filter is provided with back flush means that are coupled to said second opposite surface of said micro filter.

16. The method according to claim 15, wherein said back flush means comprise a controllable valve that releases a pressurized gas onto said second opposite surface of said micro filter.

17. The method according to claim 15, wherein said back flush means comprise a flow with a peristaltic pump onto said second opposite surface of said micro filter.

18. The method according to claim 1, wherein said micro filter has an average pore size of between 5 and 200 microns together with a pore size distribution within a standard deviation of between 0.1 and 5 microns around said average pore size.

19. The method according to claim 1, wherein said micro spheres have an average particle size of between 5 and 150 microns, together with a particle size distribution within a standard deviation of at most 25%, and said particle size distribution is more than 85% below the average pore size of said micro filter.

* * * * *

UNITED STATES PATENT AND TRADEMARK OFFICE
CERTIFICATE OF CORRECTION

| | | |
|---|---|---|
| PATENT NO. | : 11,786,881 B2 | Page 1 of 1 |
| APPLICATION NO. | : 16/605991 | |
| DATED | : October 17, 2023 | |
| INVENTOR(S) | : Lucie Anne Aude Leduc et al. | |

It is certified that error appears in the above-identified patent and that said Letters Patent is hereby corrected as shown below:

In the Specification

Column 1, Line 9, delete "PCT/IB2018/052960" and insert -- PCT/IB2018/052690 --

Signed and Sealed this
Twelfth Day of December, 2023

Katherine Kelly Vidal
*Director of the United States Patent and Trademark Office*